(12) United States Patent
Janich et al.

(10) Patent No.: US 12,390,261 B2
(45) Date of Patent: Aug. 19, 2025

(54) ELECTROSURGICAL INSTRUMENT AND ELECTROSURGICAL SYSTEM WITH AN ELECTROSURGICAL GENERATOR

(71) Applicant: OLYMPUS WINTER & IBE GMBH, Hamburg (DE)

(72) Inventors: Fabian Janich, Potsdam (DE); Anne Kwik, Berlin (DE); Frank Breitsprecher, Berlin (DE); Jens Krüger, Eichwalde (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 938 days.

(21) Appl. No.: 17/488,882

(22) Filed: Sep. 29, 2021

(65) Prior Publication Data

US 2022/0133387 A1 May 5, 2022

(30) Foreign Application Priority Data

Oct. 30, 2020 (DE) .......................... 102020128692.9

(51) Int. Cl.
*A61B 18/00* (2006.01)
*A61B 18/12* (2006.01)

(52) U.S. Cl.
CPC ............ *A61B 18/1206* (2013.01); *A61B 2018/00178* (2013.01); *A61B 2018/00589* (2013.01); *A61B 2018/00601* (2013.01); *A61B 2018/00625* (2013.01); *A61B 2018/00684* (2013.01); *A61B 2018/0091* (2013.01)

(58) Field of Classification Search
None
See application file for complete search history.

(56) References Cited

U.S. PATENT DOCUMENTS

| | | | |
|---|---|---|---|
| 2004/0034340 A1* | 2/2004 | Biscup ................... | A61B 18/20 606/1 |
| 2007/0083193 A1* | 4/2007 | Werneth ............... | A61B 5/7445 606/41 |
| 2009/0248007 A1 | 10/2009 | Falkenstein et al. | |
| 2011/0098695 A1* | 4/2011 | Brannan ................ | A61B 18/18 606/33 |

(Continued)

FOREIGN PATENT DOCUMENTS

WO 2011/032729 A1 3/2011

OTHER PUBLICATIONS

Wikipedia, "Datenstruktur", https://de.wikipedia.org/w/index.php?title=Datenstruktur&oldid=204946904, Jul. 15, 2021, pp. 1-6.

(Continued)

*Primary Examiner* — Linda C Dvorak
*Assistant Examiner* — Nicholas S Borsch
(74) *Attorney, Agent, or Firm* — Oliff PLC (57) ABSTRACT

An electrosurgical instrument with at least one active electrode for effecting an electrosurgical treatment with an instrument data memory. Furthermore, the electrosurgical instrument has a connector for a connecting cable or a connected connecting cable including supply lines for supplying the active electrode with a high-frequency alternating current required for an electrosurgical treatment. The instrument data memory has at least one read-write area to which usage and status data can be written by an electrosurgical generator.

14 Claims, 6 Drawing Sheets

(56) References Cited

U.S. PATENT DOCUMENTS

| | | | |
|---|---|---|---|
| 2012/0265189 A1* | 10/2012 | Davis .................... | A61B 18/02 |
| | | | 606/22 |
| 2019/0105096 A1* | 4/2019 | Elliott ................ | A61B 18/1233 |
| 2020/0078083 A1* | 3/2020 | Sprinkle ............ | A61B 18/1206 |

OTHER PUBLICATIONS

Jul. 15, 2021 Office action issued in German Patent Application No. 10 2020 128 692.9.

* cited by examiner

```
// 
// Variables
Set Variable(Activation State, Activation Energy (J), activationEnergy_000, Self-Refreshing)
Set Variable(Plain, 0, activationCount_001, No Options)
//
// Write to instrument                                              Dataset #0
Write To Instrument(activationEnergy_000, Energy, activationEnergy_000)  Data to be written
//                                                                  Tag
// Read from instrument                                             Dataset #1
Read From Instrument(activationCount_001, activationCount_001)
                                                                    Destination to store read data
```

Fig. 6

ELECTROSURGICAL INSTRUMENT AND ELECTROSURGICAL SYSTEM WITH AN ELECTROSURGICAL GENERATOR

The invention relates to an electrosurgical instrument and an electrosurgical system with an electrosurgical generator for supplying high-frequency alternating current to an electrosurgical instrument.

An electrosurgical system generally comprises an electrosurgical generator for generating the high-frequency alternating current. As a general rule, the electrosurgical generator has two or more outputs where an electrosurgical instrument can be connected, and a high-frequency AC voltage is provided between these outputs during operation. In addition, an electrosurgical generator generally comprises a high-voltage power supply that generates direct current during operation, and a high-frequency part that is connected to the high-voltage power supply and generates a high-frequency alternating current from the direct current during operation.

Typically, different electrosurgical instruments can be connected to the electrosurgical generator for different tasks that have different requirements regarding the generator depending on the respective electrosurgical instrument.

Electrosurgery can be used for cutting, coagulating (obliterating) and/or vaporizing biological tissue, i.e. body tissue. High-frequency alternating currents with a frequency between 0.2 MHz and 3 MHz are typically used in electrosurgery. Electrosurgical instruments are typically handheld instruments that a surgeon can use to coagulate, ablate and/or cut body tissue.

To this end, the electrosurgical instruments are supplied with high-frequency electrical energy, by means of which tissue can be coagulated or cut in a targeted manner. The high-frequency electrical energy is supplied by the electrosurgical generator and applied to the body tissue by means of the electrosurgical instrument that is appropriate in the respective case. Depending on what the electrosurgical instrument is used for, specific current and voltage curves are required; these current and voltage curves are made available to the physician for selection at the electrosurgical generator in the form of operating modes (also referred to as modes). These operating modes are permanently stored in the electrosurgical generator.

A simple programmable supply device for an electrosurgical instrument is known from WO 2011/032729 A1. The simple programmability results from defined possible states of a state machine, which, however, also limit the flexibility of the supply device.

The invention is based on the task of creating an electrosurgical instrument that can be operated flexibly and safely with an electrosurgical system.

To this end, the invention proposes an electrosurgical instrument, an electrosurgical system and an electrosurgical generator which can each individually and in combination with each other, on the one hand, allow for a very flexible operating mode, and, on the other hand, allow for operating modes that are tailored to a particular application and/or to a particular electrosurgical instrument.

An electrosurgical instrument according to the invention comprises at least one active electrode for effecting electrosurgical treatment and an instrument data memory. Furthermore, the electrosurgical instrument has a connector for a connecting cable or a connected connecting cable comprising supply lines for supplying the active electrode with a high-frequency alternating current required for an electrosurgical treatment. The electrosurgical instrument further comprises at least one data interface for reading data from the data memory and for writing data to the data memory. The data interface may be configured for wired or wireless data exchange between an electrosurgical generator and the electrosurgical instrument. The instrument data memory is preferably partitioned and preferably has at least one read-write partition (read-write area) and one configuration area (Config Area); of these, usage and status data can be written to the read-write partition.

A connected electrosurgical generator can write usage and status data to the read-write partition during operation of the electrosurgical instrument. This makes it possible to ensure safe operation of the electrosurgical instrument with an electrosurgical generator. Usage and status data may include e.g. activation and mating times, activation energies, fault conditions, or remaining activation cycles of the electrosurgical instrument. The definition of the usage and status data to be stored can be stored completely in a read-only area of the instrument data memory, so that even after a new electrosurgical generator has been launched on the market, adjustments to the usage and status data are possible via the programming of the electrosurgical instrument.

The instrument data memory of the electrosurgical instrument preferably contains data sets with structured data which contains references to operating specifications stored in a generator data memory of an electrosurgical generator. Such an electrosurgical instrument can therefore contain the necessary information that allows for an operating mode that is adapted to the respective electrosurgical instrument, without said operating mode having to be completely defined by the electrosurgical instrument.

For the data sets with structured data which contains references to operating specifications stored in a generator data memory of an electrosurgical generator, the instrument data memory of the electrosurgical instrument preferably has a further partition; however, this partition only offers a read function, not a write function during operation of the electrosurgical instrument. Accordingly, the instrument data memory preferably has a read-only area as a further partition. The data sets with structured data stored in the read-only area of the electrosurgical instrument fit a data structure in a generator data memory of an electrosurgical generator, which can be used to operate the electrosurgical instrument and which can be made up of a plurality of data sets with structured data. The structured data contains references to specific operating specifications from a plurality of operating specifications stored in the generator data memory of the electrosurgical generator, and defines those specific operating specifications, such as control commands or parameter values, that are to be applied to the respective operation of the electrosurgical instrument in a particular operating mode. During operation of the electrosurgical generator, the references defined by the structured data are called up by a processor according to an operating program that is being executed at that time and translated into operating specifications that the processor can then apply in connection with the operating program. This will be explained in more detail below in connection with the description of the electrosurgical generator.

The electrosurgical instrument is preferably a hand-held instrument with a handle and a shaft, upon which the active electrode is arranged. The data memory is preferably located in the handle of the electrosurgical instrument.

The instrument data memory of the electrosurgical instrument is preferably non-volatile, but re-writable. This is advantageous because current status and usage data regarding the electrosurgical instrument can be written to such data memory, and this status and usage data is retained even when the electrosurgical instrument is not in use.

Preferably, at least the structure of the read-write area of the instrument data memory is defined by a data allocation table that is preferably stored on an electrosurgical generator for operating the electrosurgical instrument.

The electrosurgical instrument is preferably part of an electrosurgical system that comprises, in addition to the electrosurgical instrument, also an electrosurgical generator to which the electrosurgical instrument is connected during operation. The electrosurgical generator has a processor and at least one generator data memory in which an operating program for controlling the operation of the electrosurgical generator in combination with the electrosurgical instrument is stored. Independently of the connection of an electrosurgical instrument, a theoretical arbitrary number of operating specifications are stored in the generator data memory of the electrosurgical generator, which can be called up by the operating program and can thus potentially be applied and influence the operation of the electrosurgical generator, but which do not define any fixed operating sequences. The operating specifications can, on the one hand, be control commands, command strings and/or conditional strings, but, on the other hand, also parametric data, such as values for the output voltage, output currents, output power, time settings, threshold values, error conditions, etc.

The operating specifications stored in the generator data memory can be understood as a library of any plurality of potentially applicable control instructions that can be accessed by the operating program. However, these operating specifications are not accessed directly, so that the operating program and the operating specifications as content of the generator data memory do not yet determine the mode of operation of the electrosurgical generator.

Rather, a data structure, in which arbitrary data sets with structured data are stored, is also provided. The structured data contains references to concrete operating specifications, such as control commands or parameter values stored in the generator data memory. During operation of the electrosurgical generator, the references defined by the structured data are called up by the processor according to the operating program that is being executed at that time, and the associated operating specifications are applied by the operating program.

Thus, the specific mode of operation of the electrosurgical generator depends on three different types of stored data, namely
  on the data in the generator data memory which defines the operating program;
  on the potentially applicable operating specifications in the generator data memory, which define e.g. control commands or parameter values, and some of which are specifically applied because of the references contained in the data structure;
  on the data sets with structured data stored in the data structure, which contain the references to specifically applicable operating specifications and which are called up by the processor during the course of the operating program and translated into specifically applicable operating specifications.

The three types of data—operating program, operating specifications and structured data of the data structure—can be changed and specified independently, with the limitation that the data formats are compatible. Thus, the mode of operation of the electrosurgical generator in a respective operating mode can be changed by modifying the operating program stored in the generator data memory, or by modifying the operating specifications that are also stored in the generator data memory, or by modifying the structured data in the data structure, or also through a combination of these changes. The data structure can be available in either the generator data memory or the instrument data memory, or in both data memories.

The generator data memory preferably contains a data allocation table that at least defines the structure of the read-write area of the instrument data memory of the electrosurgical instrument.

The electrosurgical instrument preferably contains the non-volatile instrument data memory (e.g. an EEPROM or similar), but no processor. On the instrument data memory of the surgical instrument, in addition to the usage and status data stored in the read-write area, there is a data set, preferably stored in the read-only area, with structured data containing references to operating specifications and, if applicable, parameter values. The structured data of this data set is compatible with the data structure of the electrosurgical generator and may form the data structure of the electrosurgical generator or a part of the data structure of the electrosurgical generator.

The data structure can thus be part of a generator data memory, which is a physical component of the electrosurgical generator, or it is formed by the content of the instrument data memory of the electrosurgical instrument, or by a combination of a generator data memory of the electrosurgical generator and the instrument data memory of the electrosurgical instrument. Preferably, the data structure is stored at least partially in a separate partition of the data memory of the electrosurgical instrument, namely the read-only area.

The processor of the electrosurgical generator is configured, in combination with the operating program, to read and write to the instrument data memory of the electrosurgical instrument. The preferably provided partitioning of the memory of the electrosurgical instrument ensures that the data structure in the partition forming the read-only area can only be read, but not written to, by the electrosurgical generator during the normal electrosurgical operation. On the other hand, the electrosurgical generator can—and should—be able to write to the partition with the read-write area, namely to write status and usage data regarding the respective electrosurgical instrument. To this end, a data allocation table is stored in the generator data memory.

The writing of status and usage data is preferably done by defining corresponding references to control commands within the structured data. The data is then stored according to the data allocation table defined in the generator (tag1+value1, tag2+value2, ...).

The reading of status and usage data is also done via the data allocation table. For example, after an electrosurgical instrument has been connected to the electrosurgical generator, the electrosurgical generator reads the read-write partition of the instrument data memory and decodes the status and usage data according to the data allocation table, and can act on it independently, e.g. to display instrument information.

The processor of the electrosurgical generator can be configured by the operating program to read the instrument data memory of the electrosurgical instrument—in particular the read-only area and the read-write area—after the electrosurgical instrument has been connected to the electrosurgical generator and before the electrosurgical generator is operated in an operating mode. The processor of the electrosurgical generator can be configured by the operating program to transfer the data set or the data sets or the structured data contained in the data set or the data sets into a data structure that is stored in the generator data memory of the electrosurgical generator.

The processor of the electrosurgical generator can alternatively be configured by the operating program to read the instrument data memory of the electrosurgical instrument while the operating program is running—i.e. while the electrosurgical generator is being operated in an operating mode. Thus, no computer program or algorithm is stored in the instrument data memory of the surgical instrument, and the structured data is neither readable as a computer program nor as an algorithm associated with a program.

The structured data—including the structured data stored in the partition making up the read-only area of the data memory of the electrosurgical instrument—preferably contains parameterized references. The references enable the targeted calling up of operating specifications, such as control commands, by means of the operating program.

The structured data is preferably available in a memory-efficient binary format consisting of a 1-byte reference and additional information required for the operating specification.

The electrosurgical system preferably has a programming interface, or several programming interfaces, by means of which the content in particular of the generator data memory and in particular of the data structure can be programmed with the structured data. Accordingly, it may also be provided that the operating program in the generator data memory can be changed via a programming interface, for example by way of a software update of the electrosurgical generator via USB.

The invention also proposes a method for operating an electrosurgical instrument according to the invention by means of an electrosurgical generator, according to which method, during operation of the electrosurgical instrument, the electrosurgical generator writes usage and status data relating to the electrosurgical instrument to the read-write area of the data memory.

Preferably, operating specifications and a data structure are provided in memory areas of the generator data memory of the electrosurgical generator that are independent of each other, wherein the data structure contains references to the operating specifications, and the processor indirectly accesses individual operating specifications, while the operating program is running, by first accessing references in the data structure and subsequently retrieving that operating specification or those operating specifications to which a respective reference refers.

The data structure is preferably read from an instrument data memory of an electrosurgical instrument, and preferably after an electrosurgical instrument has been connected and before it is used. The data sets with structured data contained in the data structure on the electrosurgical instrument can be transferred into a data structure that is stored on an electrosurgical generator.

A further aspect of the invention is an electrosurgical generator for operating the electrosurgical instrument. The electrosurgical generator has connections for connecting the electrosurgical instrument as well as a processor and at least one generator data memory, which
  contains first data that defines an operating program for controlling the operation of the electrosurgical generator in conjunction with the electrosurgical instrument;
  contains second data that defines the operating specifications that can be called up by the operating program and influence the operation of the electrosurgical generator, but which do not define any fixed operating sequences; and
  contains third data, which defines a data structure containing data sets with structured data that contains references to individual operating specifications.

The electrosurgical generator is configured to read usage and status data stored in the data memory of the electrosurgical instrument when an electrosurgical instrument according to the invention is connected to the electrosurgical generator, and to store usage and status data in a read-write area of the instrument data memory of the electrosurgical instrument during operation with an electrosurgical instrument according to the invention.

Such an electrosurgical generator can easily be used with a variety of different electrosurgical instruments, wherein the adaptation to the respective electrosurgical instrument can be made solely by means of corresponding entries in the data structure which represent references, without the operating specifications in the generator data memory of the electrosurgical generator having to be changed. In particular, it is possible to make the operation of a specific electrosurgical instrument also dependent on status and usage data stored on this electrosurgical instrument.

The invention will now be explained in more detail based on exemplary embodiments referencing the figures. The figures show the following.

Figure 1:
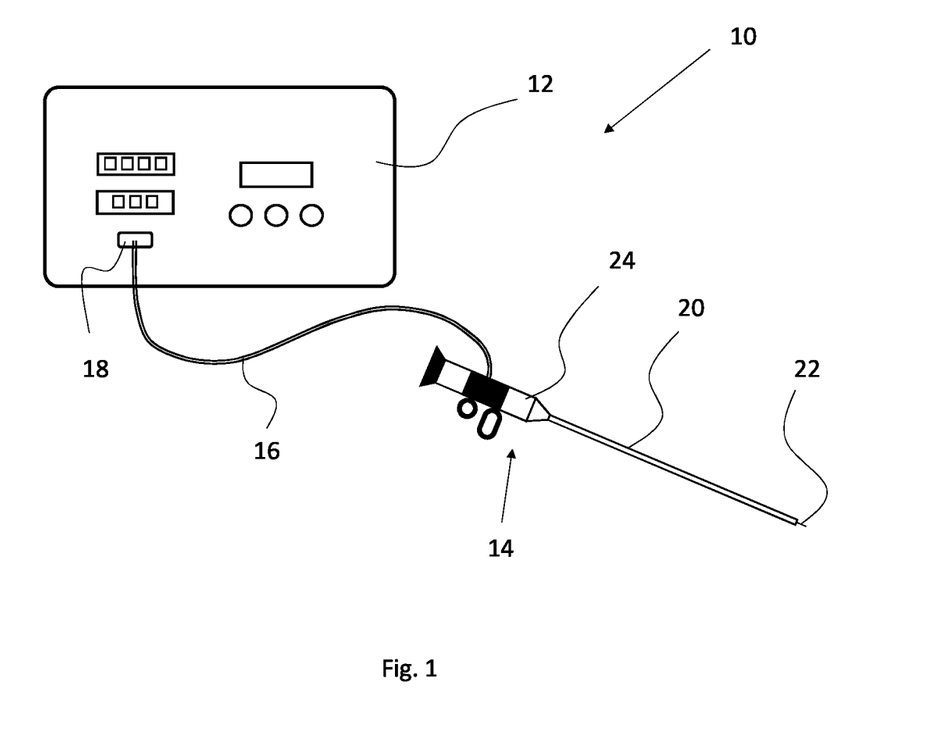
FIG. 1: An electrosurgical system with an electrosurgical generator and an electrosurgical instrument connected thereto.

FIG. 1 shows an electrosurgical system 10. The electrosurgical system 10 comprises an electrosurgical generator 12 and an electrosurgical instrument 14. Via a connecting cable 16, the electrosurgical instrument 14 is connected to electrical outputs and inputs 18 of the electrosurgical generator 12.

The electrosurgical instrument 14 has a shaft 20, at the end of which is an active electrode 22. The shaft 20 is attached to a handle 24 of the electrosurgical instrument 14.

The electrosurgical instrument 14 features a writable, preferably non-volatile instrument data memory 26. The instrument data memory 26 can be an EEPROM (electrically erasable programmable read-only memory), for example. An EEPROM is a non-volatile data memory that can be read, written, and write-protected. The data memory 26 is, for example, located in the handle 24 of the electrosurgical instrument 14.

The connecting cable 16 contains both supply lines 28 and 30 as well as at least one data line 32 for reading data from the data memory 26 and for writing data to the instrument data memory 26. The supply lines 28 connect the active electrode 22 and another neutral electrode, that is not described in more detail, to the electrical outputs 18.1 and 18.2 of the electrosurgical generator 12. Via the data line 32, the instrument data memory 26 is connected to a corresponding connection 18.3 of the electrosurgical generator 12. This is shown schematically in FIG. 2.

Figure 2:
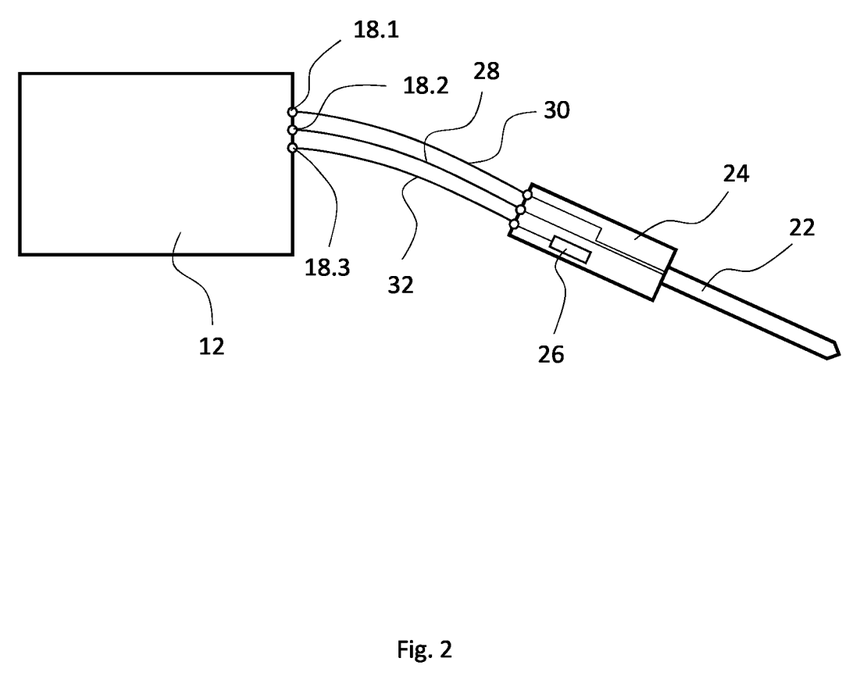
FIG. 2: An electrosurgical instrument.

The data line 32 in the connecting cable 16 as well as the connection 18.3 can be a multicore and/or multi-pole line/connection. In addition to or instead of the data line 32, a wireless interface may be provided for the data transfer from the electrosurgical instrument 14 to the electrosurgical generator 12. Such a wireless interface may, for example, be a Bluetooth interface, an NFC interface or an RFID interface.

The data memory 26 of the electrosurgical instrument 14 is partitioned and, in particular, has a partition forming a read-write area from which the usage and status data can be read or to which usage and status data can be written. The reading and writing of the usage and status data is done via a data allocation table. The data allocation table is preferably stored in a generator data memory 72 of the electrosurgical generator 12 for operating the electrosurgical instrument 14.

Usage and status data to be stored in the partition of the data memory 26 forming the read-write area can be, for example, activation and mating times, activation energies, fault conditions or remaining activation cycles. This usage and status data is to be stored completely in the electrosurgical instrument 14 so that even after an electrosurgical generator has been launched on the market, adjustments to the usage and status data to be stored are possible via the programming of the electrosurgical instrument 14. The instrument data memory 26 may be partitioned. In this case, the memory model must fit into the existing partitioning of the data memory 26 of the electrosurgical instrument 14. This is shown in Table 1 below. Specifically, an area of definable size is available, the so-called read-write area, in which the usage and status data can be stored.

TABLE 1

| | Area | Description |
|---|---|---|
| 1 | Legacy Tables | Mode information for legacy systems |
| 2 | Config Area | Description of the subsequent areas (e.g. size information) |
| 3 | Read-only Area | Structured data that, in addition to the operating mode, primarily also defines the status and usage data to be stored. |
| 4 | Write-Protect Block Alignment | Chip-specific attachment data for the read data area |
| 5 | Read-write Area | Status and usage data for exchange between instrument and electrosurgical generator |
| 6 | Write-Protect Block Alignment | Chip-specific attachment data for the read and write data area |
| 7 | Next Table(s) | Memory space for additional mode tables |
| 8 | Last Config Area | Final configuration |

The read-write area is an area for the memory model according to the invention, so that status and usage data can be stored.

To meet the above-mentioned requirements, the instrument data memory 26 of the electrosurgical instrument 14 is provided with a memory model defined by a data allocation table, as shown in Table 2 below. The data allocation table must be known to all reading and recording devices, but, according to the exemplary embodiment, is not stored in the instrument data memory 26 of the electrosurgical instrument 14. The data allocation table is preferably stored in the generator data memory 72 of the electrosurgical generator 12.

TABLE 2

Exemplary Data Allocation Table

| Name | ID | Description | Size [Byte] | Type |
|---|---|---|---|---|
| NONE | 0 | No data | 0 | N/A |
| RTOU | 1 | Counter #1 for ultra-sound activations | 2 | 2 byte unsigned integer counter |
| TIMESTAMP | 2 | Timestamp (e.g. last mating time) | 4 | 4 byte unsigned integer timestamp |
| ENERGY | 3 | Energy (e.g. supplied energy of the last activation) | 4 | 4 byte unsigned integer energy |
| ACTIVATIONTIME | 4 | Activation time (e.g. time of the last activation) | 4 | 4 byte unsigned integer number |
| GENERIC | 5 | General data | 4 | 4 byte float value |
| ACTIVATION_COUNT | 6 | Counter #2 for ultra-sound activations | 4 | 4 byte unsigned integer counter |

RTOU is the abbreviation for "remaining times of use"

Specifically, the data allocation table defines different identifiers (tags) that, in turn, define
 the size of the subsequent data (e.g. 4 bytes), and
 the type of the subsequent data (e.g. timestamp).

The data to be exchanged and stored can be defined with a programming interface 82 (see later in the text) and finally stored in the read-write area of the instrument data memory 26 of the electrosurgical instrument 14 as a sequence of identifier (tag) and value. The sum of the data determines the size of the read-write area and is preferably stored in the configuration area (Config Area) of the electrosurgical instrument during programming and partitioning of the instrument data memory 26 of the electrosurgical instrument 14. The electrosurgical generator 12 can read the data of the read-write area. The identifiers (tags) define which data the electrosurgical generator 12 should read and process and which data it should update.

Figure 6:
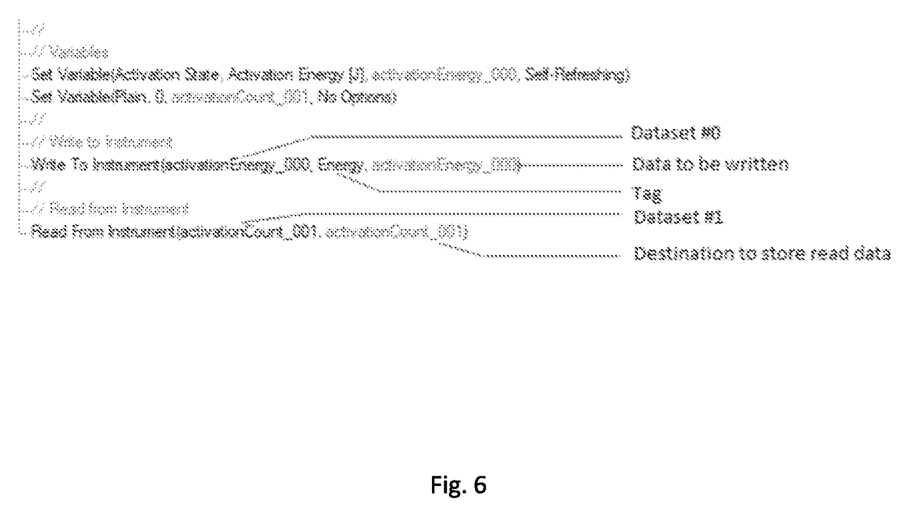
FIG. 6: An example of a definition of usage and status data to be stored in the electrosurgical instrument.

FIG. 6 shows an example of a definition of usage and status data by means of a programming interface 82 described below.

Figure 3:
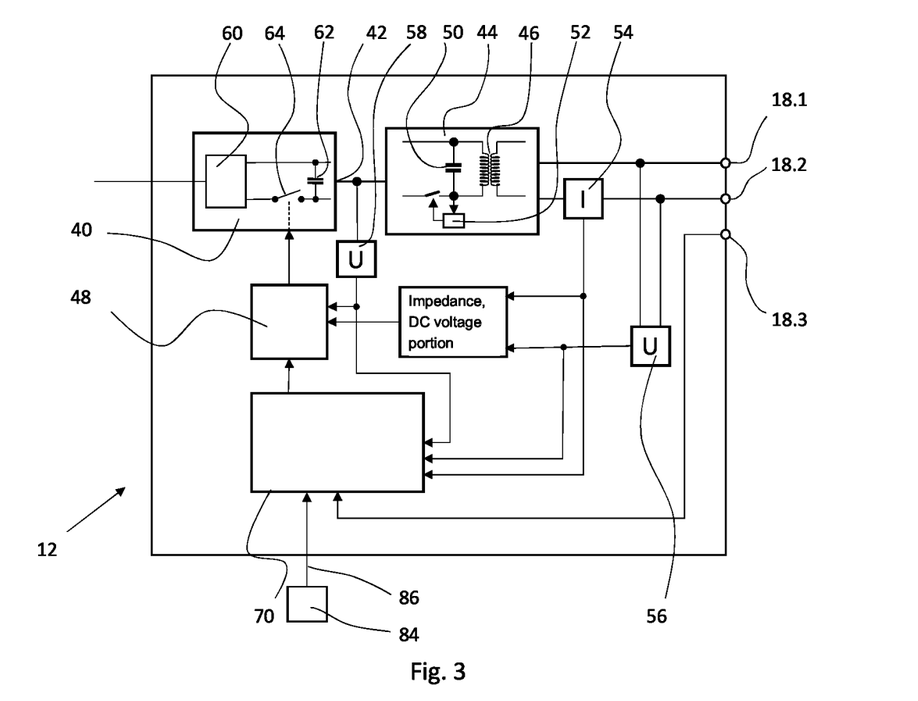
FIG. 3: A schematic diagram of an electrosurgical generator.

During operation, the AC output voltage that is to be supplied to the active electrode 22 and a return electrode of the electrosurgical instrument 14 for the operation of the electrosurgical instrument 14 is provided by the electrosurgical generator 12. As shown in FIG. 3, the electrosurgical generator 12 has a high-voltage power supply 40 for this purpose, which can be connected to the usual public power grid, for example, and provides a high-frequency direct current with DC output voltage at its output 42. This direct output current is supplied to a high-frequency part 44 of the electrosurgical generator 12. The high-frequency part 44 of the electrosurgical generator 12 serves as an inverter and produces a high-frequency AC output voltage that is supplied to the outputs 18.1 and 18.2 of the electrosurgical generator 12 via an output transformer 46 of the high-frequency part 44. The electrosurgical instrument 14 can be connected to the outputs 18.1 and 18.2 of the electrosurgical generator 12, as shown in FIGS. 1 and 2.

To control the AC output voltage of the electrosurgical generator 12, a generator control unit 48 is provided that controls the AC output voltage at the outputs 18.1 and 18.2 of the electrosurgical generator 12 based on a maximum AC output voltage value such that, for example, a preset maximum output voltage value is not exceeded during operation.

The AC output voltage of the electrosurgical generator 12—and therefore also the alternating output current and the output power—can be controlled by a generator control unit 48.

The generator control unit 48 controls the high-voltage power supply 40 in dependence on maximum values defined by a respective operating mode and on current values of the AC output voltage, the peak output voltage, the alternating output current, the DC voltage portion of the AC output voltage or the DC output voltage detected during operation by detection units 54, 56 and 58, or on a combination of values of these parameters.

The specific maximum values and the time sequence for generating the AC output voltage of the electrosurgical generator 12 and their dependence on detected momentary values depend on the respective operating mode (mode) in which the electrosurgical generator 12 is currently being operated.

An operating mode is, for example, called up through the actuation of a corresponding switch by a user, for example a foot-operated switch 84.

In a respective operating mode, the operation of the electrosurgical generator 12 is controlled by a processor 70 in combination with an operating program 74 stored in the generator data memory 72. The processor 70 generates—under the control of the operating program 74—the maximum values for the different operating parameters, for example—such as the AC output voltage, the alternating output current, the output power, but also the DC voltage portion of the AC output voltage, wherein the respective current value of these parameters is detected during operation of the electrosurgical generator 12.

The processor 70 is connected to the generator data memory 72, in which the operating program 74 for the electrosurgical generator 12 is stored.

During execution of the operating program 74 stored in the generator data memory 72, the processor 70 accesses, at locations stored in the operating program, operating specifications 76, such as data representing values for operating parameters and/or control commands, which are stored in the generator data memory 72 for a respective operating mode. The operating specifications 76 specify, for example, specific values for the DC output voltage of the high-voltage power supply or the AC output voltage, the alternating output current of the high-frequency part, or similar data. However, operating specifications 76 stored in the generator data memory 72 also include specific control commands, such as "if" or "while", or "true" or "false". That way the data and control commands stored as operating specifications 76 can be combined by way of references in a data structure 78, for example, into control instructions such as "compare the current value of the AC output voltage to the amount 200 and return "true" if the current value of the voltage is smaller than or equal to 200 and "false" if the current value is greater than 200".

Other data and control commands can, for example, result in the control instruction that the maximum DC output voltage of the high-voltage power supply shall be 100 Volt.

Figure 4:
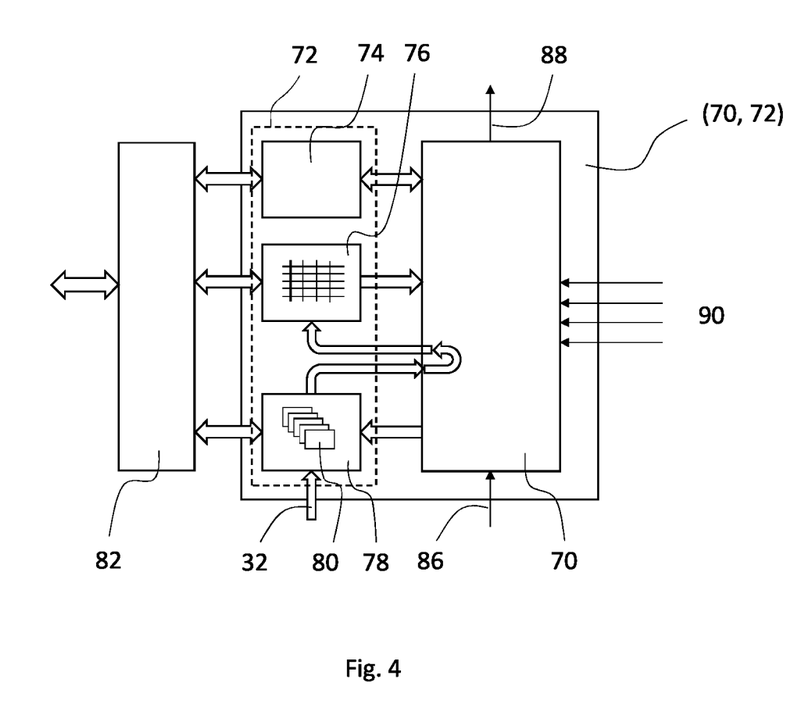
FIG. 4: A schematic illustration of a processor in combination with a generator data memory of the electrosurgical generator of FIG. 3.

During operation, the processor 70 does not access the operating specifications 76 directly, but calls up the data structure 78 at the respective points of the operating program; references referring to corresponding operating specifications 76 are stored for a respective operating mode in said data structure 78; see e.g. FIG. 4. The references may, for example, be numbers, in particular 1-byte binary numbers, since they require little memory space. In this case, the operating specifications 76 can be organized in the form of a table, in which each reference (i.e. for example each hexadecimal number) is assigned the corresponding control commands or data.

A plurality of data sets 80 that each contain one reference or several references which, due to the structure of the respective data set—in particular the order in which the references are stored—can be assigned line numbers, are stored in the data structure 78, so that different operating modes can be implemented. The line numbers can be addresses within the structured data of a data set, which the processor 70 can access under the control of the operating program. The references assigned to a line number refer to specific operating specifications 76 in the generator data memory 72 and cause the processor 70 to read the corresponding operating specifications from the generator data memory 72, after the processor 70 has first accessed the vector address stored in the data structure 78 and designated by the associated line number. The operating specifications 76 may be control instructions, control commands or parameter values, which the operating program 74 is to apply at the respective point of the operating program where the operating program 74 contains a reference to a line number in the data structure 78.

References to operating specifications 76 in the generator data memory 72 are stored in the data structure 78 in an ordered sequence. The structure of a respective data set in the data structure 78 makes it possible to assign line numbers, like addresses, within the data structure 78 to the references so that, for example, jumps or returns to references in the data structure 78 are possible and not only a strictly sequential processing of the references by the operating program. The line numbers can serve as vector addresses within the structured data in the data structure 78, which the processor 70 accesses under the control of the operating program. The references assigned to the line numbers refer to corresponding operating specifications in the generator data memory 72. The operating specifications can be control specifications, namely e.g. individual control commands, composite control instructions, or parameter values. The control specifications control the operation of the electrosurgical generator 12 in the respective operating mode. The control specifications can also be control commands that cause other references in the data structure 78 to be called up. However, this is only possible within a data set with structured data, which data belongs to a respective operating mode.

The parameterized references are preferably represented by hexadecimal numbers that, together, form structured data of a data set 80. A data set belongs to an operating mode and can contain the following, for example:

| 006F | 11 |             |
|------|----|-------------|
| 0070 | 36 | 02 30 00 C8 00 |
| 0076 | 12 |             |
| 0077 | 0F | 04 64 00    |
| 0078 | 56 |             |
| 007C | 4B | 03 02       |
| 007F | 13 |             |

The numbers shown in italics are line numbers that were generated while the data set 80 was being read and are not stored in the data memory 26 of the electrosurgical instrument 14; instead, they are generated by the operating program itself in accordance with the order of the references in a corresponding data set. The line numbers are the result of the order of the references (i.e. their structure) in a respective data set. The line numbers represented in the example by the numbers shown in italics are simply numbers in ascending order in accordance with the length of the structured data. The numbers shown in bold serve as references (or pointers), each of which refers to a specific operating specification 76 in the generator data memory 72, namely—in the illustrated example—to control commands. Thus, "11", for example, refers to the control command "IF", "36" refers to a comparison that is specified by the following assigned numbers "02 30 00 C8 00", "12" refers to the control command "THEN", "0F" refers to a control command for setting a parameter value specified by the following assigned numbers "04 64 00", and "56" refers to the control command "ELSE".

The respective operating specification 76 called up by means of the parameterized reference also shows which additional information (such as "02 30 00 C8 00" in the example above) is also relevant.

The operating program 74 can read and translate the example described above as follows:

```
11-if -> no additional information required
36-comparison -> 5 characters of additional information required (02 = 1 character
type of comparison, 30 00 = 2 characters number 1, C8 00 = 2 characters number 2)
12-then -> no additional information required
0F-set initial value -> 3 characters additional information (04 = 1 character which
initial value; 64 00 = 2 characters set value)
. . .
Translated, this can mean "Compare whether number 1 (30 00) is greater than number 2
(C8 00). If the result is TRUE, set voltage to 100 V (64 00), else . . ."
```

The binary numbers shown in the example as hexadecimal numbers (and herein referred to in short as "hexadecimal numbers") in a respective data set 80 thus represent first of all references, based on which the operating program 74 can access specific operating specifications 76 in the generator data memory 72. The hexadecimal numbers stored in a data set in a structured (ordered) manner represent the aforementioned references to operating specifications 76 stored in the generator data memory 72, such as control commands and parameters, which, due to the structure of the data set 80, can be assigned line numbers that, as such, do not need to be explicitly stored in the data set 80, but that can be generated by the operating program 74 during the import of a respective data set 80.

The binary numbers stored in a respective data set 80 and shown as hexadecimal numbers in the example serve as pointers, each of which refers to a specific operating specification 76 in the generator data memory 72 of the electrosurgical generator 12 so that the corresponding hexadecimal number (i.e. the reference in the structured data) is linked to a corresponding operating specification 76 in the generator data memory 72 of the electrosurgical generator 12. Thus, these hexadecimal numbers are used to designate a corresponding operating specification 76 in the generator data memory 72 of the electrosurgical generator 12. These hexadecimal numbers are therefore a kind of pointer for guiding the operating program to the operating specifications 76 in the generator data memory 72 of the electrosurgical generator 12, where the operating program 74 can, during its execution, in each case call up an operating specification for the operating program 74. The calling up of the references is controlled by the operating program 74, resulting in the operating program 74 calling up those operating specifications 76 in the generator data memory 72 to which the references refer. Jumps within the references that are identified by their sequence or line numbers are also possible. Via the memory entries in the generator data memory 72 corresponding to it, the structured data in a data set 80 can thus be translated into specific operating specifications 76 for the operating program 74.

In the data set shown by way of example above, the entries in the first column ("006F, 0070, 0076 . . . ") are the line numbers to which the operating program 74 can refer. The line numbers are not stored in the data memory 26 of the electrosurgical instrument 14, but are generated by the operating program 74 itself, since the line numbers are simply numbers in ascending order in accordance with the length of the structured data:

0070 36 02 30 00 C8 00 (data length=6, i.e. the next address is 0076)

0076 12 (data length=1, i.e. the next address is 0077)

The entries in each line ("11, 36 02 30 00 C8 00, 12 . . . ") refer to positions of memory entries in the generator data memory 72 that contain operating specifications 76. The entry in the generator data memory 72 labeled 11 may be an operating specification representing an "IF" instruction, for example, while the entry labeled 12 may be a "THEN" instruction. The "IF" instruction and the "THEN" instruction are each one operating specification. Based on the associated operating specifications 76 in the generator data memory 72, the hexadecimal numbers "36 02 30 00 C8 00" that, in the structured data of the illustrated data set, are located between 11 and 12 can be translated into a control instruction, such as "Compare the last read value of the voltage (30 00) with the number 200 (C8 00) and return "TRUE" if the voltage is smaller than or equal to 200, else return "FALSE". When the operating program 74 calls up the memory entries for the string "0F 04 64 00" from the generator data memory 72 at the address "0077" (generated by the operating program 74), this could denote a setting for the electrosurgical generator 12; the setting may e.g. be that a maximum value for the DC output voltage (0F 04) is set to 100V (64 00).

Thus, the operation of the electrosurgical generator 12 in a respective operating mode depends first of all on the operating program 74 stored in the generator data memory 72. However, in addition, the operating behavior of the electrosurgical generator 12 in a respective operating mode also depends on the data set 80 in the data structure 78 called up for a respective operating mode as well as on the operating specifications 76 also stored in the generator data memory 72.

The advantage of such an electrosurgical generator 12 is that new operating modes can easily be defined by generating new data sets 80 in the data structure 78, and that a single operating mode can, for example, be changed solely by changing the corresponding data set 80 in the data structure 78, without the operating program 74 in the generator data memory 72 or the operating specifications 76 in the generator data memory 72 having to be changed. On the other hand, global parameters, such as any potential control instructions that might be available or operating parameters depending on the electrosurgical generator 12, such as its maximum AC output voltage or a minimum permissible DC output voltage, can be stored as operating specifications 76 in the generator data memory 72, where they can, if need be, also be changed centrally for all possible operating modes at once.

Figure 5:
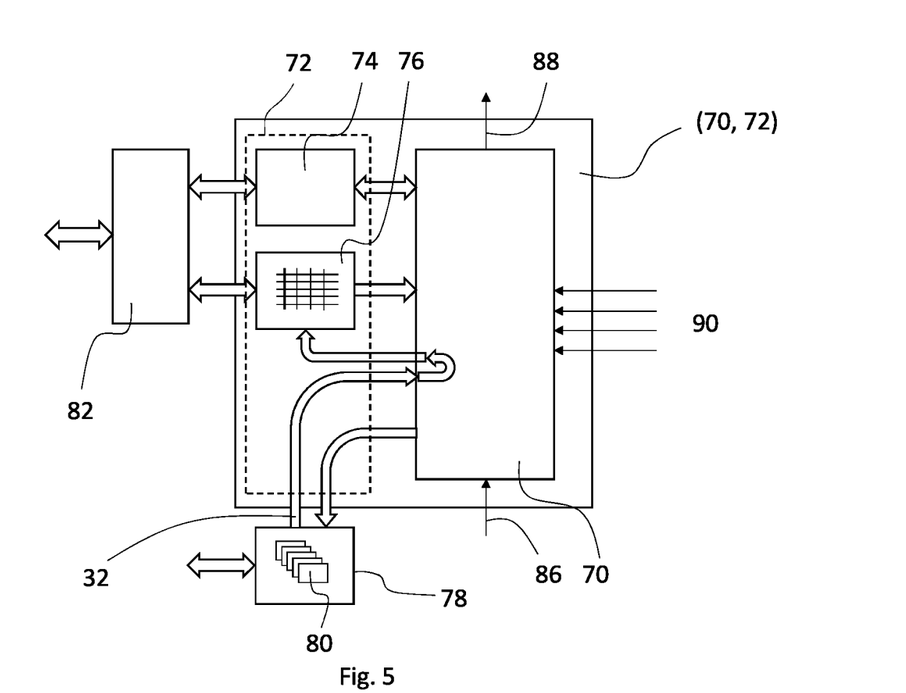
FIG. 5: A schematic illustration of an alternative configuration of the processor in combination with a generator data memory of the electrosurgical generator of FIG. 3.

Another advantage of the electrosurgical generator 12 is that a data set 80, the structured data of which indirectly defines an operating mode suitable for the electrosurgical instrument 14, can also be stored in an electrosurgical instrument 14; see FIG. 5. Specifically, the instrument data memory 26 of the electrosurgical instrument 14 can contain a data set 80 with structured data that is compatible with the data structure 78 and, just like other structured data in the data structure 78, indirectly defines a respective operating mode by means of corresponding references to specific operating specifications 76 in the generator data memory 72. For example, in the instrument data memory 26, one or several data sets 80 with structured data are then stored in a read-only area, and status and usage data for a specific electrosurgical instrument 14 are stored in a read-write area.

The electrosurgical generator 12 is configured in such a way that, when an electrosurgical instrument 14 is connected, the electrosurgical generator 12 will, in each case, first read the instrument data memory 26 of the electrosurgical instrument 14—if available—and enter the structured data from the data set stored in the data memory 26 into the data structure 78. Thus, an operating mode precisely tailored to the respective electrosurgical instrument 14 will be available to the electrosurgical generator 12 during operation. At the same time, the electrosurgical generator 12 also reads the status and usage data from the read-write area of the instrument data memory 26 of the electrosurgical instrument 14.

In order to allow access to the content of the instrument data memory 26 of the electrosurgical instrument 14, at least the data line 22 with a corresponding connection 18.3 is provided. As an alternative or in addition, a wireless interface, such as a Bluetooth interface or an NFC interface, may be provided for accessing the content of the instrument data memory 26 of the electrosurgical instrument 14.

When the structured data is transferred from the instrument data memory 26 of the electrosurgical instrument 14 into a corresponding data set in the data structure 78 of the electrosurgical generator 12, the line numbers specified by the structure of the structured data in the instrument data memory 26 can, if applicable, be generated to match the operating program of the electrosurgical generator 12.

It is a great advantage that the data set 80 stored in the read-only area of the instrument data memory 26 only contains references ordered in a structured manner (pointers to further memory entries 76 in the generator data memory 72), but does not directly contain any control instructions or operating parameters for a respective operating mode since the control instructions and the operating parameters are centrally stored as operating specifications 76 in the generator data memory 72 of the electrosurgical generator 12.

Alternatively, the electrosurgical generator 12 can also be configured such that it directly reads out the instrument data memory 26 of the electrosurgical instrument 14 during operation—i.e. during the execution of the operating program 74. This is the case in the example shown in FIG. 5. In this case, the structured data of the data set in the data memory 26 of the electrosurgical instrument 14 does not need to be transferred into the data structure 78 of the electrosurgical generator 12 first. However, the line numbers must match the corresponding call-ups in the operating program and the entries representing the operating specifications in the generator data memory 76 in this case. The electrosurgical generator 12 will preferably always read the status and usage data from the read-write area of the instrument data memory 26 right after an electrosurgical instrument has been connected to the electrosurgical generator 12.

An advantage of an electrosurgical system 10 of the type described herein is that different data that defines the operation of the electrosurgical generator 12 can be managed independently of one another. Thus, the operating program 74 stored in the generator data memory 72 is stored independently of the operating specifications 76 in the generator data memory 72. Operating specifications 76 are, in turn, stored independently of the structured data in the data structure 78.

For programming the operating program 74, the operating specifications 76 and the data structure 78 with the structured data, a programming interface 82 is provided that is preferably configured in such a way that it grants different rights to different users. Thus, different rights can be assigned for programming the operating program 74 that is stored in the generator data memory 72, for entering the operating specifications 76 that are also stored in the generator data memory 72, and for the structured data that is stored in the data structure 78 in the generator data memory 72 and/or in the instrument data memory 26. This way, it can in particular be ensured that changes to the operating specifications 76 or changes to the operating program 74 can only be made by developers who are familiar with the respective electrosurgical generator 12. The operating program 74 and the operating specifications 76 can thus be programmed by developers who are familiar with the respective electrosurgical generator 12, while a developer who is familiar with the electrosurgical instrument 14 can define the operating modes for an electrosurgical instrument 14 by creating a corresponding data set 80 with structured data. Preferably, data sets created by a developer who is familiar with the electrosurgical instrument 14 are stored in the instrument data memory 26 of the respective electrosurgical instrument 14, while further operating modes can also be stored directly in the data structure 78 on the electrosurgical generator 12. To this end, the electrosurgical generator 12 can have a USB programming interface, for example.

Either the data line 32 in the connecting cable 16 with a corresponding interface, or—as an alternative or in addition—a wireless interface, such as a Bluetooth interface or an NFC interface, is available for the structured data and status and usage data stored in the instrument data memory 26 of the respective electrosurgical instrument 14. The structured data from the data set 80 as well as the status and usage data in the instrument data memory 26 of the electrosurgical instrument 14 can then be transferred into the data structure 78 of the electrosurgical generator when the electrosurgical instrument 14 is connected.

This is, in particular, relevant with regard to different electrosurgical instruments 14, since the electrosurgical instruments 14 might be integrated by other developers than the electrosurgical generator 12. The developers of the electrosurgical generator 12 can store all the specific parameter data and control commands that are important for the electrosurgical generator 12—if need be in dependence on the operating program 74 stored in the generator data memory 72—as operating specifications in the generator data memory 72. Such parameter values can, for example, be maximum or minimum permissible values for the DC output voltage, the AC output voltage, etc.

Independently of this, developers of an electrosurgical instrument 14 can use the structured data in the data set in the instrument data memory 26 of the electrosurgical instrument to specify in detail how a specific operating mode can be executed for this electrosurgical instrument 14 within the framework of the operating specifications 76 in the generator data memory 72 as read out by the operating program 24 in the generator data memory 72. The developers of the electrosurgical instrument 14 do not need to give any further consideration to the operating program 74 and the potentially applicable operating specifications 76. Instead, the developers of the electrosurgical instrument 14 can accept these operating specifications provided for the respective electrosurgical generator 12.

While the structured data in the read-only area of the instrument data memory 76 is already generated by a developer by means of a programming interface 82 during the manufacturing of the electrosurgical instrument, for example, the data stored in the read-write area of the instrument data memory 26 is preferably written to the instrument data memory 26 according to the data allocation table by the electrosurgical generator 12 after each use of the electrosurgical instrument 14, and thus updated.

A programming interface 82 is available to the developers of an electrosurgical instrument 14 for defining an operating mode for the respective electrosurgical instrument 14, and for defining data to be exchanged with the electrosurgical instrument 14 and to be stored in the data memory 26 of the electrosurgical instrument 14.

Status and usage data stored in the read-write area of the electrosurgical instrument can be read by the electrosurgical generator when the electrosurgical instrument 14 is connected to the electrosurgical generator 12, or during its operation. The reading of status and usage data is done using the data allocation table. The status and usage data is stored in the read-write area as a tag and value sequence (see Table 3: Sample data set for stored status and usage data). The electrosurgical generator 12 thus sequentially reads the read-write area of the instrument data memory 26 and first finds a tag (e.g. 0x01). According to the data allocation table, the electrosurgical generator 12 now knows how much data follows and which data it is (e.g. remaining ultrasound activations with a length of 1 byte). The electrosurgical generator 12 then finds another tag (e.g. 0x03). According to the data allocation table, the electrosurgical generator 12 now knows how much data follows and which data it is (e.g. supplied activation energy with a length of 2 bytes). This is repeated until the generator finds the end tag 0x00.

TABLE 3

Sample data set for stored status and usage data

| Address in read-write area | Memory content | Description |
| --- | --- | --- |
| 0x0000 | 0x01 | 1st tag<br>0x01 = Subsequent data defines the remaining ultrasound activations; the length of the data is 1 byte (see data allocation table) |
| 0x0001 | 0xff | 1, data<br>0xff = 255 remaining ultrasound activations |
| 0x0002 | 0x03 | 2nd tag<br>0x03 = Subsequent data defines the supplied activation energy; the length of the data is 2 bytes (see data allocation table) |

TABLE 3-continued

Sample data set for stored status and usage data

| Address in read-write area | Memory content | Description |
| --- | --- | --- |
| 0x0003 | 0xff | 2nd data |
| 0x0004 | 0xff | 0xffff = 65535 mJ were supplied during the last activation |
| 0x0005 | 0x00 | 3rd tag<br>0x00 = No further data |

Which status and usage data is to be stored is defined in the structured data in the instrument data memory 26 of the electrosurgical instrument 14. For this purpose, specific parameterizable references are available for storing status and usage data. An example for writing the remaining ultrasound activations as well as the supplied activation energy can be found in Table 4: Example for defining status and usage data to be written. The column "Resulting structured data" is inserted at the appropriate place into the structured data defining the operating mode and finally stored in the read area of the electrosurgical instrument.

TABLE 4

Example for defining status and usage data to be written

| Reference | Parameter 1 | Parameter 2 | Resulting structured data |
| --- | --- | --- | --- |
| Write to instrument | RTOU | 255 | 0x4D 0x01 0xFF |
| Write to instrument | Activation energy | 65535 | 0x4D 0x03 0xFF 0xFF |

The data to be exchanged with the electrosurgical instrument 14 and stored in the data memory 26 of the electrosurgical instrument 14 can thus be defined via the programming interface 82 (see FIG. 1) and finally stored in the read-write area as a sequence of identifier (tag) and value. Table 5 below shows an example:

TABLE 5

Sample data set with stored usage and status data (in italics)

| Partition | Data | Description |
| --- | --- | --- |
| Read-write area | *0x01* | Tag 0 (0x01 = 1-byte counter ultrasound activations) |
| | *0xff* | Data 0 (0xff = 255 ultrasound activations left) |
| | *0x03* | Tag 1 (0x03 = 2 bytes activation energy) |
| | *0xffff* | Data 1 (0xffff = 65535 mJ) |
| | *0x00* | Tag 2 (0x00 = 0 byte no data) |

The sum of the data determines the size of the read-write area and is finally stored in the configuration area (Config Area) during programming and partitioning of the instrument data memory 26 of the electrosurgical instrument 14. The electrosurgical generator 12 can read the data of the read-write area. The identifiers (tags) define which data the electrosurgical generator 12 should read and process and which data it should update.

Via the programming interface 82, a developer can define the data to be exchanged between and stored in the electrosurgical generator 12 and the electrosurgical instrument 14. FIG. 6 shows an example of a definition of usage and status data by means of the programming interface 82.

Via the programming interface 82, a developer can also fully define an operating mode for a respective electrosurgical instrument 14. This definition includes, for example, all current and voltage parameter values as well as timing specifications and transition conditions for the operation of the electrosurgical instrument. Thus, the operating mode can be developed with the aid of an easy-to-use tool virtually without any software development knowledge by a developer for an electrosurgical instrument. The programming interface 82 provides to the developer a number of parameter sets that the developer can use to define different phases, for example the initial incision phase, the cutting phase, the coagulation phase, but also short-circuit or power monitoring for the respective electrosurgical instrument. A development tool belonging to the programming interface 82 generates a memory space-saving set of structured data from the specifications, wherein said set of data forms a data set that can be stored in the data memory 26 of the electrosurgical instrument 14 in a non-volatile manner.

If a new operating mode for an electrosurgical instrument defined by structured data in a data set 80 also requires a change of the operating program 74 in the generator data memory 72 or of the operating specifications 76 in the generator data memory 72, such changes can, for example, be made by a developer who is familiar with the electrosurgical generator 12 via a programming interface 82. This way it can be ensured that the structured data that defines an operating mode is compatible with the operating specifications 76 in the generator data memory 72 and the operating program 74 in the generator data memory 72. The developer of the electrosurgical instrument can consult the developer familiar with the electrosurgical generator in this regard. As a result, it is ensured that a developer who is not familiar with the electrosurgical generator—e.g. a developer for an electrosurgical instrument—cannot create erroneous operating specifications or change the operating program in a way that causes unintended effects or errors.

When an electrosurgical instrument 14 is connected to the electrosurgical generator 12, the electrosurgical generator 12 reads the instrument data memory 26 in the electrosurgical instrument 14 and interprets the structured data in the data set 80 stored therein using the operating specifications 76 in the generator data memory 72, so that the current and voltage curves including any timing requirements and other conditions defined in those operating specifications 76 are applied. This allows for reduced development times and costs. For the most part, the electrosurgical instrument 14 can be integrated independently of an electrosurgical generator 12. In addition, this allows for a shorter time-to-market, since the operating modes can also be developed and finalized after the introduction of an electrosurgical generator 12. Optimizations of an operating mode and new operating modes can be easily introduced by means of updated or new electrosurgical instruments 14. An operating mode for an electrosurgical instrument can be defined with almost no software development knowledge.

If the electrosurgical system 10 is to be operated with an electrosurgical instrument 14 connected to the electrosurgical generator 12, the appropriate operating mode will already be available once the electrosurgical instrument 14 has been connected, since the associated data sets 80 with the structured data can be read by the instrument data memory 26 of the electrosurgical instrument 14. Therefore, a user will, for example, only have to actuate a switch 84, in order to operate the electrosurgical instrument 14 in the appropriate operating mode of the electrosurgical generator 12. After connecting the electrosurgical instrument 14, the user does not need to set or program anything.

The switch 84 is functionally connected to the processor 70 of the electrosurgical generator 12 via a line 86, so that the execution of the operating program 74 stored in the generator data memory 72 can be started and stopped through the actuation of the switch 84. The switch 84 may be a foot-operated switch, but may also be a hand-operated switch, that is, for example, located on the electrosurgical instrument 14. A wireless control connection can be provided instead of the line 86.

Another alternative to a switch 84 is an automatic start of the operating program, which a user can activate in advance. In this case, the electrosurgical instrument first outputs a small measurement voltage in order to detect tissue contact (current flow) with the aid of said measurement voltage. If tissue contact—i.e. current flow—is detected, the actual operating program for the electrosurgical instrument will be called up. If the tissue contact disappears, the actual operating program for the electrosurgical instrument will be ended, and a small measurement voltage will once again be output so that a new tissue contact can be detected with the aid of said measurement voltage.

Under the control of the operating program 74, the processor 70 indirectly accesses individual operating specifications 76 in the generator data memory 77 during the use of an operating mode by first accessing the references in the data structure 78 and subsequently calling up the operating specification or operating specifications referred to by the respective reference.

Depending on the content of the generator data memory 72 and on the data structure 78 as well as on signals 90 coming from the detection units 54, 56 and 58, the processor 70 generates control signals 88 for the generator control unit 46.

REFERENCE NUMBERS 10 electrosurgical system
12 electrosurgical generator
14 electrosurgical instrument
16 connecting cable
18.1, 18.2 electrical outputs
18.3 connection
20 shaft
20.1, 20.2 outputs
22 active electrode
24 handle
26 instrument data memory
28, 30 supply lines
32 data line
40 high-voltage power supply
42 output
44 high-frequency part
46 output transformer
48 generator control unit
50 capacitor
52 synchronizing circuit
54 output current detection unit
56 AC output voltage detection unit
58 DC output voltage detection unit
60 high-voltage rectifier circuit
62 output capacitor
64 switch
70 processor
72 generator data memory
74 operating program 76 operating specifications
78 data structure
80 data set
82 programming interface
84 switch
86 line
88 control signals of the processor
90 signals of the detection units

The invention claimed is:

1. Electrosurgical system comprising an electrosurgical instrument, having an instrument data memory and a connection for a connecting cable or a connected connecting cable, which includes supply lines for supplying a high-frequency alternating current required for an electrosurgical treatment to at least one active electrode, and at least one data line for reading data from the instrument data memory and for writing data to the instrument data memory,
  wherein the instrument data memory has at least one read-write area where status and usage data is modifiably stored by an electrosurgical generator using a data allocation table that defines a structure of the read-write area,
  and an electrosurgical generator, to which the electrosurgical instrument is connected, wherein the electrosurgical generator has a processor and at least one generator data memory where
  first data is stored that defines an operating program for controlling the operation of the electrosurgical generator in conjunction with the electrosurgical instrument;
  second data is stored that represents operating specifications that can be called up by the operating program and influence the operation of the electrosurgical generator, but which does not define any fixed operating sequences;
  third data is stored that forms a data structure with data sets with stored structured data that contains references to operating specifications stored in the generator data memory, which allow for calling up individual references in a targeted manner by the operating program during operation; and
  fourth data is stored that forms a data allocation table for a read-write area of the instrument data memory of the electrosurgical instrument to be connected to the electrosurgical generator during operation, wherein the operating specifications and the data structure are provided independently of each other, and wherein the processor of the electrosurgical generator indirectly accesses individual operating specifications, while the operating program is running, by first accessing references in the data structure and subsequently retrieving an operating specification or those operating specifications to which a respective reference refers, and the data structure is read from the instrument data memory.

2. Electrosurgical system according to claim 1, wherein the data structure is formed by the content of a read-only area of the instrument data memory of the electrosurgical instrument.

3. Electrosurgical system according to claim 1, wherein the processor of the electrosurgical generator is configured, in combination with the operating program, to read or write to the instrument data memory of the electrosurgical instrument.

4. Electrosurgical system according to claim 1, wherein the processor of the electrosurgical generator is configured by the operating program to read the instrument data memory of the electrosurgical instrument while the operating program is running.

5. Electrosurgical system according to claim 1 further comprising one programming interface or several programming interfaces, by means of which the content of the generator data memory and of the data structure can be programmed.

6. Electrosurgical instrument for an electrosurgical system, wherein the electrosurgical instrument comprises at least one active electrode for effecting an electrosurgical treatment, an instrument data memory, and a connection for a connecting cable or a connected connecting cable, which features supply lines for supplying a high-frequency alternating current required for an electrosurgical treatment to the active electrode, and at least one data line for reading data from the instrument data memory and for writing data to the instrument data memory,
  wherein the instrument data memory has at least one read-write area where status and usage data is modifiably stored by an electrosurgical generator using a data allocation table that defines the structure of the read-write area, wherein the instrument data memory is partitioned and features a first partition making up a read-write area and a second partition making up a read-only area, and wherein the data sets with structured data are stored in the partition of the instrument data memory that makes up the read-only area.

7. Electrosurgical instrument according to claim 6, wherein the instrument data memory contains data sets with structured data, said data containing references to operating specifications stored in a generator data memory of an electrosurgical generator.

8. Electrosurgical instrument according to claim 6, wherein the instrument data memory of the electrosurgical instrument is configured in such a way that an electrosurgical generator can, while the electrosurgical instrument is in operation, write usage and status data regarding the electrosurgical instrument into a partition of the data memory that makes up the read-write area.

9. Electrosurgical instrument according to claim 6, wherein the instrument data memory is a non-volatile memory.

10. Electrosurgical instrument according to claim 6, wherein the electrosurgical instrument is a hand-held instrument with a handle and a shaft upon which the active electrode is arranged.

11. Electrosurgical instrument according to claim 10, wherein the instrument data memory is located in the handle of the electrosurgical instrument.

12. Electrosurgical generator for an electrosurgical system, comprising connections for connecting an electrosurgical instrument for the electrosurgical system, wherein the electrosurgical instrument has at least one active electrode for effecting an electrosurgical treatment, with an instrument data memory and with a connection for a connecting cable or a connected connecting cable, which features supply lines for supplying a high-frequency alternating current required for an electrosurgical treatment to the active electrode, and at least one data line for reading data from the instrument data memory and for writing data to the instrument data memory,
  wherein the instrument data memory has at least one read-write area where status and usage data is modifiably stored by an electrosurgical generator using a data allocation table that defines a structure of the read-write area, and the electrosurgical generator having a processor and at least one generator data memory, which contains an operating program for controlling the operation of the electrosurgical generator in conjunction with the electrosurgical instrument;

contains operating specifications that can be called up by the operating program and influence the operation of the electrosurgical generator, but which do not define any fixed operating sequences;

contains a data structure with data sets with structured data that contains references to operating specifications stored in the generator data memory; and contains a data allocation table for a read-write area of an instrument data memory of an electrosurgical instrument to be connected to the electrosurgical generator during operation;

wherein the processor is configured, in combination with the operating program, to write usage and status data regarding the electrosurgical instrument, when the electrosurgical instrument is in operation, into a partition making up the read-write area of the instrument data memory, and wherein the operating specifications and the data structure are provided independently of each other, and wherein the processor of the electrosurgical generator indirectly accesses individual operating specifications, while the operating program is running, by first accessing references in the data structure and subsequently retrieving an operating specification or those operating specifications to which a respective reference refers, and the data structure is read from the instrument data memory.

13. Method for operating an electrosurgical system according to claim 1, wherein the electrosurgical generator writes usage and status data regarding the electrosurgical instrument, when the electrosurgical instrument is in operation, into a partition of the data memory that makes up the read-write area.

14. Method according to claim 13, wherein, after connection and prior to the use of an electrosurgical instrument, the data structure and status and usage data are read from the data memory of the electrosurgical instrument, and data sets with structured data contained in the data structure on the electrosurgical instrument are transferred to a data structure that is stored on an electro-surgical generator.

* * * * *